(12) United States Patent
Kang et al.

(10) Patent No.: US 11,434,527 B2
(45) Date of Patent: Sep. 6, 2022

(54) METHOD FOR DETECTING MYCOPLASMA USING MITOCHONDRIAL DNA AS INTERNAL CONTROL SAMPLE

(71) Applicants: The Asan Foundation, Seoul (KR); University of Ulsan Foundation for Industry Cooperation, Ulsan (KR)

(72) Inventors: Eun Ju Kang, Gyeonggi-do (KR); Yeon Mi Lee, Seoul (KR)

(73) Assignees: The Asan Foundation, Seoul (KR); University of Ulsan Foundation for Industry Cooperation, Ulsan (KR)

(*) Notice: Subject to any disclaimer, the term of this patent is extended or adjusted under 35 U.S.C. 154(b) by 20 days.

(21) Appl. No.: 17/055,551

(22) PCT Filed: May 17, 2019

(86) PCT No.: PCT/KR2019/005898
§ 371 (c)(1),
(2) Date: Nov. 13, 2020

(87) PCT Pub. No.: WO2019/221537
PCT Pub. Date: Nov. 21, 2019

(65) Prior Publication Data
US 2021/0115505 A1   Apr. 22, 2021

(30) Foreign Application Priority Data
May 18, 2018 (KR) .................. 10-2018-0057283

(51) Int. Cl.
*C12Q 1/68* (2018.01)
*C12Q 1/6851* (2018.01)
*C12Q 1/6888* (2018.01)

(52) U.S. Cl.
CPC ......... *C12Q 1/6851* (2013.01); *C12Q 1/6888* (2013.01); *C12Q 2545/101* (2013.01); *C12Q 2565/125* (2013.01)

(58) Field of Classification Search
CPC ....................................................... C12Q 1/68
(Continued)

(56) References Cited

U.S. PATENT DOCUMENTS

2008/0187916 A1* 8/2008 Ikonomi ................ C07K 14/30
                                                              435/6.12
2011/0091885 A1* 4/2011 Schmitt ................ C12Q 1/6881
                                                              435/6.19

FOREIGN PATENT DOCUMENTS

CN        107475389        12/2017
KR    10-2009-0081039       7/2009
(Continued)

OTHER PUBLICATIONS

Uphoff & Drexler, Detecting mycoplasma contamination in cell cultures by polymerase chain reaction, Methods Mol Biol. 2011;731: 93-103. doi: 10.1007/978-1-6 1779-080-5_8.*
(Continued)

*Primary Examiner* — Aaron A Priest
(74) *Attorney, Agent, or Firm* — Morrison & Foerster LLP (57) ABSTRACT

The present invention provides a method for detecting *mycoplasma*, which can directly confirm whether a cell is infected with *mycoplasma*, by simultaneously amplifying DNA extracted from lysing a host cell infected with *mycoplasma*, and mitochondrial DNA in the cytoplasm of the host cell. According to the method of the present invention, by directly using the DNA inside the host cell, the DNA of *mycoplasma* bound around the nucleus of the host cell can be used as an amplification target, thereby increasing detection sensitivity. In addition, since the mitochondrial DNA
(Continued)

inside the host cell is used as an amplification target of an internal control sample, whether the sample has been sampled in an appropriate amount can be confirmed in a convenient manner, and furthermore, by comparing the band size between the internal control sample and the *mycoplasma* DNA, the degree of *mycoplasma* infection can be quantitatively confirmed.

8 Claims, 1 Drawing Sheet

Specification includes a Sequence Listing.

(58) Field of Classification Search
 USPC ....................................................... 435/6.12
 See application file for complete search history.

(56) References Cited

FOREIGN PATENT DOCUMENTS

| KR | 10-2013-0128334 | 11/2013 |
| KR | 10-2015-0007049 | 1/2015 |
| WO | WO 1996/036735 | 11/1996 |

OTHER PUBLICATIONS

Uphoff et al., "Comparative PCR Analysis for Detection of Mycoplasma Infections In Continuous Cell Lines," In Vitro Cell Dev Biol—Animal (2002) 38:79-85.

Uphoff et al., "Detecting mycoplasma contamination in cell cultures by polymerase chain reaction," Methods in Mol Medicine (2004) 88:319-326.

* cited by examiner

METHOD FOR DETECTING MYCOPLASMA USING MITOCHONDRIAL DNA AS INTERNAL CONTROL SAMPLE

STATEMENT OF GOVERNMENTAL SUPPORT

The invention was made with government support under Serial No. NRF-2020M3A9E4036527 entitled "Development of commercialized pluripotent stem cells based on mitochondrial genome" from the National Research Foundation (NRF) (Republic of Korea).

CROSS-REFERENCE TO RELATED APPLICATION

This application is a national stage application under 35 U.S.C. § 371 of International Application No. PCT/KR2019/005898, filed internationally on May 17, 2019, which claims priority to and the benefit of Korean Patent Application No. 10-2018-0057283, filed on May 18, 2018, the disclosures of which are incorporated herein by reference in their entirety.

INCORPORATION BY REFERENCE OF SEQUENCE LISTING

The present application is being filed along with a Sequence Listing in electronic format. The Sequence Listing is provided as a file entitled 717572002800SeqList.TXT, created Nov. 13, 2020, which is 2,344 bytes in size. The information in the electronic format of the Sequence Listing is incorporated by reference in its entirety.

BACKGROUND

1. Field of the Invention

The present invention relates to a method for detecting *mycoplasma*, which can sensitively determine whether the infection of *mycoplasma* has occurred by using mitochondrial DNA isolated from the cell pellet of a cell infected with *mycoplasma* as an internal control sample.

2. Discussion of Related Art

*Mycoplasma* is known to be the simplest primitive cell that lives independently among the known organisms. Since it was discovered in 1898, *mycoplasma* has been reported as a pathogen that can be found in a wide range of nature such as animals including humans, birds, sewage or the like, and it can cause inflammation mainly in mammals and birds. *Mycoplasma* lacks a cell wall, and the outer wall is composed only of a cell membrane, and thus it is known to have specific antibiotic susceptibility unlike general microorganisms having a cell wall.

Since *mycoplasma* is capable of self-replication in artificial media, it has been reported that it inhabits a culture medium during cell culture and cells to be cultured can be infected as host cells around the nucleus. Specifically, it is known that during cell culture, a range of 5% to 35% of cell lines are mainly contaminated by 6 types of *mycoplasma* such as *Mycoplasma arginini, M. fermentans, M. hyorhinis, M. orale* or *Acholeplasma laidlawii*. For the main causes of such contamination, it may be caused by animal tissue used in the primary culture, serum used during culture, the experimenter or the like, and contamination may spread to other cell lines due to cross-contamination of cell lines in the laboratory.

Accordingly, the development of *mycoplasma* detection methods is in progress for the purpose of confirming whether contamination by *mycoplasma* or infection of *mycoplasma* has occurred in an experimental environment dealing with *mycoplasma* or in a patient suspected of *mycoplasma* infection, and various commercial kits have been developed. Since the existing *mycoplasma* detection methods using such commercial kits use a method of detecting *mycoplasma* that is contaminated in a cell culture solution or secreted from host cells infected by *mycoplasma*, it can merely detect the presence or absence of *mycoplasma* that is infected in a culture medium, and ultimately, it cannot directly confirm whether the infection of *mycoplasma* has occurred inside cells that are being cultured, and thus it has a limitation that the sensitivity of detection is reduced. In addition, when conventional commercialized detection kits are used, for quantitative analysis during *mycoplasma* detection, quantitative analysis is performed based on the number of amplification cycles during a PCR. Since it is greatly affected by the background, DNA bands may appear during electrophoretic analysis after the PCR, even when the DNA of *mycoplasma* that is used as an amplification target is low in quantity or not included, and thus there is a limitation that the reliability of detection results is low. Therefore, for confirmation of the presence of *mycoplasma* infected in the cell and quantitative analysis thereof, even though it is expected that a method of directly lysing a cell and confirming whether *mycoplasma* is detected against DNA in the cell can improve reliability, studies related thereto have not been reported yet.

As such, the present inventors have spent efforts to develop a *mycoplasma* detection method that is cheaper with increased detection sensitivity by directly confirming whether the DNA of *mycoplasma* infected in a host cell is included, and as a result, the present invention was completed by confirming that sensitivity was improved during the detection of *mycoplasma* and detection experiments could also be carried out at a lower cost compared to existing commercialized kits, through a PCR amplification method comprising lysing a host cell infected with *mycoplasma* and using the same as a PCR template and simultaneously using mitochondrial DNA of the host cell as an internal control sample.

RELATED ART DOCUMENTS

Non-Patent Documents (Non-Patent Document 1) Uphoff CC, Drexler HG. (2002) Comparative PCR analysis for detection of *mycoplasma* infections in continuous cell lines. *In Vitro Cell Dev Biol Animl.* 38(2): 79-85.

(Non-Patent Document 2) Uphoff CC, Drexler HG. (2004) Detecting *Mycoplasma* contamination in cell cultures by polymerase chain reaction. *Methods Mol Med.* 88: 319-326.

SUMMARY OF THE INVENTION

Accordingly, an object of the present invention is to provide a method for detecting *mycoplasma*, in which sensitivity is improved compared to existing *mycoplasma* detection methods, and the degree of infection can be quantitatively confirmed through establishing an internal control sample.

In order to achieve the above object, the present invention provides a method for detecting *mycoplasma*, comprising the following steps i) to iii):

i) extracting DNA from a host cell isolated from a subject suspected of being infected with *mycoplasma*;

ii) performing polymerase chain reaction (PCR) using the DNA extracted in step i) as a template; and iii) confirming a DNA band by electrophoresis of the PCR product performed in step ii).

In one preferred exemplary embodiment of the present invention, the host cell of step i) may be a cell derived from human.

In one preferred exemplary embodiment of the present invention, the PCR of step ii) may amplify a target sequence using a primer set for amplifying *mycoplasma* DNA; and a primer set for amplifying mitochondrial DNA of a host cell.

In addition, the primer set for amplifying *mycoplasma* DNA may comprise a forward primer comprising a nucleotide sequence of SEQ ID NO: 1; a forward primer comprising a nucleotide sequence of SEQ ID NO: 2; a forward primer comprising a nucleotide sequence of SEQ ID NO: 3; a forward primer comprising a nucleotide sequence of SEQ ID NO: 4; a forward primer comprising a nucleotide sequence of SEQ ID NO: 5; a forward primer comprising a nucleotide sequence of SEQ ID NO: 6; a reverse primer comprising a nucleotide sequence of SEQ ID NO: 7; a reverse primer comprising a nucleotide sequence of SEQ ID NO: 8; and a reverse primer comprising a nucleotide sequence of SEQ ID NO: 9.

In addition, the primer set for amplifying mitochondrial DNA of a host cell may comprise a forward primer comprising a nucleotide sequence of SEQ ID NO: 10; and a reverse primer comprising a nucleotide sequence of SEQ ID NO: 11.

In addition, the present invention provides a method for providing information for diagnosing *mycoplasma* infection, comprising the following steps i) to iii):

i) extracting DNA from a host cell isolated from a subject suspected of being infected with *mycoplasma*;

ii) performing polymerase chain reaction (PCR) using the DNA extracted in step i) as a template; and iii) determining that the subject is infected with *mycoplasma*, if the amplification of *mycoplasma* DNA is confirmed in the PCR of step ii).

In one preferred exemplary embodiment of the present invention, the PCR of step ii) may be performed using a forward primer comprising a nucleotide sequence of SEQ ID NO: 1; a forward primer comprising a nucleotide sequence of SEQ ID NO: 2; a forward primer comprising a nucleotide sequence of SEQ ID NO: 3; a forward primer comprising a nucleotide sequence of SEQ ID NO: 4; a forward primer comprising a nucleotide sequence of SEQ ID NO: 5; a forward primer comprising a nucleotide sequence of SEQ ID NO: 6; a reverse primer comprising a nucleotide sequence of SEQ ID NO: 7; a reverse primer comprising a nucleotide sequence of SEQ ID NO: 8; a reverse primer comprising a nucleotide sequence of SEQ ID NO: 9; a forward primer comprising a nucleotide sequence of SEQ ID NO: 10; and a reverse primer comprising a nucleotide sequence of SEQ ID NO: 11.

In one preferred exemplary embodiment of the present invention, the confirmation of the amplification of *mycoplasma* DNA in step iii) may confirm that DNA having a size of 500 bp has been amplified.

In addition, the present invention provides a kit for detecting *mycoplasma*, comprising the following a) to c):

a) a cell lysis buffer;

b) a primer set for amplifying *mycoplasma* DNA; and c) a primer set for amplifying mitochondrial DNA of a host cell.

In one preferred exemplary embodiment of the present invention, the b) primer set for amplifying *mycoplasma* DNA may comprise a forward primer comprising a nucleotide sequence of SEQ ID NO: 1; a forward primer comprising a nucleotide sequence of SEQ ID NO: 2; a forward primer comprising a nucleotide sequence of SEQ ID NO: 3; a forward primer comprising a nucleotide sequence of SEQ ID NO: 4; a forward primer comprising a nucleotide sequence of SEQ ID NO: 5; a forward primer comprising a nucleotide sequence of SEQ ID NO: 6; a reverse primer comprising a nucleotide sequence of SEQ ID NO: 7; a reverse primer comprising a nucleotide sequence of SEQ ID NO: 8; and a reverse primer comprising a nucleotide sequence of SEQ ID NO: 9.

In one preferred exemplary embodiment of the present invention, the c) primer set for amplifying mitochondrial DNA of a host cell may comprise a forward primer comprising a nucleotide sequence of SEQ ID NO: 10; and a reverse primer comprising a nucleotide sequence of SEQ ID NO: 11.

Further, the present invention provides a composition for detecting *mycoplasma* infection, comprising:

a forward primer comprising a nucleotide sequence of SEQ ID NO: 1;

a forward primer comprising a nucleotide sequence of SEQ ID NO: 2;

a forward primer comprising a nucleotide sequence of SEQ ID NO: 3;

a forward primer comprising a nucleotide sequence of SEQ ID NO: 4;

a forward primer comprising a nucleotide sequence of SEQ ID NO: 5;

a forward primer comprising a nucleotide sequence of SEQ ID NO: 6;

a reverse primer comprising a nucleotide sequence of SEQ ID NO: 7;

a reverse primer comprising a nucleotide sequence of SEQ ID NO: 8; and a reverse primer comprising a nucleotide sequence of SEQ ID NO: 9.

The present invention also provides a use of a primer set in detection or infection diagnosis of *mycoplasma*, the primer set comprising:

a forward primer comprising a nucleotide sequence of SEQ ID NO: 1;

a forward primer comprising a nucleotide sequence of SEQ ID NO: 2;

a forward primer comprising a nucleotide sequence of SEQ ID NO: 3;

a forward primer comprising a nucleotide sequence of SEQ ID NO: 4;

a forward primer comprising a nucleotide sequence of SEQ ID NO: 5;

a forward primer comprising a nucleotide sequence of SEQ ID NO: 6;

a reverse primer comprising a nucleotide sequence of SEQ ID NO: 7;

a reverse primer comprising a nucleotide sequence of SEQ ID NO: 8; and a reverse primer comprising a nucleotide sequence of SEQ ID NO: 9.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the present invention will be described in detail.

The present invention provides a method for detecting *mycoplasma*, comprising the following steps i) to iii):

i) extracting DNA from a host cell isolated from a subject suspected of being infected with *mycoplasma*;

ii) performing polymerase chain reaction (PCR) using the DNA extracted in step i) as a template; and iii) confirming a DNA band by electrophoresis of the PCR product performed in step ii).

In the *mycoplasma* detection method of the present invention, the host cell of step i) is preferably a cell derived from an animal known to be capable of being infected with *mycoplasma*, and more preferably, a cell derived from a mammal specifically, and most preferably, a cell derived from human more specifically, but is not limited thereto.

In addition, examples of the host cell of step i) may include a cultured cell, a protein, or a nucleic acid, or biological medicine including the same, tissue obtained from the brain, eye, heart, intestine, kidney, liver, lung, muscle, spleen or testis of animals or humans, or a body fluid such as blood, plasma, serum, urine, saliva, sweat, semen, mucus or the like, but are not limited thereto.

In the *mycoplasma* detection method of the present invention, it is preferable to apply a method of extracting DNA in a small amount of cells to the DNA extraction step of step i). Specifically, it is more preferable to use an intracellular mitochondrial DNA extraction method, but is not limited thereto.

In the *mycoplasma* detection method of the present invention, the PCR of step ii) may amplify a target sequence using a primer set for amplifying *mycoplasma* DNA; and a primer set for amplifying mitochondrial DNA of a host cell.

The primer set for amplifying *mycoplasma* DNA may be designed for the purpose of complementarily binding to DNA derived from *mycoplasma* infected around the nucleus of a host cell to specifically amplify the same. The primer set according to the present invention may be constructed based on a known *mycoplasma* sequence, and specifically, it is most preferable to comprise 6 forward primers and 3 reverse primers as follows: a forward primer comprising a nucleotide sequence of SEQ ID NO: 1; a forward primer comprising a nucleotide sequence of SEQ ID NO: 2; a forward primer comprising a nucleotide sequence of SEQ ID NO: 3; a forward primer comprising a nucleotide sequence of SEQ ID NO: 4; a forward primer comprising a nucleotide sequence of SEQ ID NO: 5; a forward primer comprising a nucleotide sequence of SEQ ID NO: 6; a reverse primer comprising a nucleotide sequence of SEQ ID NO: 7; a reverse primer comprising a nucleotide sequence of SEQ ID NO: 8; and a reverse primer comprising a nucleotide sequence of SEQ ID NO: 9.

In the *mycoplasma* detection method of the present invention, as a control sample for confirming that the amplification result of the cell-derived DNA can show significant reliability, mitochondrial DNA of the host cell may be induced to be amplified simultaneously with *mycoplasma* DNA. Specifically, a primer pair used to amplify the mitochondrial DNA may preferably comprise a forward primer comprising a nucleotide sequence of SEQ ID NO: 10; and a reverse primer comprising a nucleotide sequence of SEQ ID NO: 11, but are not limited thereto. More specifically, any primer sequence may be used without limitation as long as it is understood by those skilled in the art to be used for amplifying the mitochondrial DNA of a host cell that may be infected by *mycoplasma* as in humans.

As used herein, the term "primer" refers to an oligonucleotide complementary to the 5' terminal sequence and 3' terminal sequence adjacent to a target nucleic acid used in the polymerase chain reaction, and the terms "forward primer" and "reverse primer" refer to primers that bind to the 3' end and 5' end of a specific region of a gene amplified by the polymerase chain reaction, respectively.

Examples of *mycoplasma* that may be detected by the *mycoplasma* detection method of the present invention include various mycoplasmas such as *Mycoplasma arthritidis* (*M. arthritidis*), *Mycoplasma bovis* (*M. bovis*), *Mycoplasma fermentans* (*M. fermentans*), *Mycoplasma hyorhinis* (*M. hyorhinis*), *Mycoplasma neurolyticum* (*M. neurolyticum*), *Mycoplasma orale* (*M. orale*), *Mycoplasma arginini* (*M. arginini*), *Mycoplasma pirum* (*M. pirum*), *Mycoplasma pulmonis* (*M. pulmonis*) and *Mycoplasma salivarium* (*M. salivarium*), *Acholeplasma laidlawii* that cause frequent *mycoplasma* infection during in vitro cell culture, *Mycoplasma pneumonia* (*M. pneumonia*) that causes pneumonia during infection of the human body, *Mycoplasma genitalium*, *Ureaplasma urealyticum* and *Mycoplasma hominis* (*M. hominis*) that causes diseases of the genitourinary system such as non-gonococcal urethritis, but are not limited thereto.

Preferably, the *mycoplasma* detection method of the present invention may detect one or more selected from the group consisting of *Mycoplasma bovis* (*M. bovis*), *Mycoplasma fermentans* (*M. fermentans*), *Mycoplasma hyorhinis* (*M. hyorhinis*), *Mycoplasma orale* (*M. orale*), *Mycoplasma arginini* (*M. arginini*), *Acholeplasma laidlawii* and *Mycoplasma hominis* (*M. hominis*).

In addition, the present invention provides a method for providing information for diagnosing *mycoplasma* infection, comprising the following steps i) to iii):

i) extracting DNA from a host cell isolated from a subject suspected of being infected with *mycoplasma*;

ii) performing polymerase chain reaction (PCR) using the DNA extracted in step i) as a template; and iii) determining that the subject is infected with *mycoplasma*, if the amplification of *mycoplasma* DNA is confirmed in the PCR of step ii).

In the method of the present invention, since the host cell of step i) has been described above in the *mycoplasma* detection method, repeated description will be omitted.

In the method of the present invention, since the DNA extraction step of step i) has been described above in the *mycoplasma* detection method, repeated description will be omitted.

In the method of the present invention, the PCR of step ii) is preferably performed using a forward primer comprising a nucleotide sequence of SEQ ID NO: 1; a forward primer comprising a nucleotide sequence of SEQ ID NO: 2; a forward primer comprising a nucleotide sequence of SEQ ID NO: 3; a forward primer comprising a nucleotide sequence of SEQ ID NO: 4; a forward primer comprising a nucleotide sequence of SEQ ID NO: 5; a forward primer comprising a nucleotide sequence of SEQ ID NO: 6; a reverse primer comprising a nucleotide sequence of SEQ ID NO: 7; a reverse primer comprising a nucleotide sequence of SEQ ID NO: 8; a reverse primer comprising a nucleotide sequence of SEQ ID NO: 9; a forward primer comprising a nucleotide sequence of SEQ ID NO: 10; and a reverse primer comprising a nucleotide sequence of SEQ ID NO: 11. Specifically, regarding the primer sequence provided in the method of the present invention, since the *mycoplasma* detection method is already described, repeated description will be omitted.

In the method of the present invention, the amplification of *mycoplasma* DNA in step iii) can be confirmed by the size of a DNA band through electrophoresis after PCR. Specifically, when a subject suspected of being infected with *mycoplasma* is actually infected with *mycoplasma*, it may be confirmed that the DNA having a size of 500 bp is specifically amplified as a result of the PCR. Furthermore, the mitochondrial DNA of a host cell is preferably confirmed through specific amplification of DNA having a size of 300 bp.

In the method of the present invention, for the purpose of adding reliability to information for diagnosis, a PCR may be performed by further using a primer set for amplifying mitochondrial DNA. Specific examples of the primer set for amplifying mitochondrial DNA may be a forward primer comprising a nucleotide sequence of SEQ ID NO: 10; and a reverse primer comprising a nucleotide sequence of SEQ ID NO: 11.

In addition, the present invention provides a kit for detecting *mycoplasma*, comprising the following a) to c):
a) a cell lysis buffer;
b) a primer set for amplifying *mycoplasma* DNA; and
c) a primer set for amplifying mitochondrial DNA of a host cell.

Since the primer set of b) is already described above in the *mycoplasma* detection method, repeated description will be omitted.

The kit of the present invention may further include a reagent for performing an amplification reaction, for example, DNA polymerase, dNTPs, buffers and the like. In addition, the kit of the present invention may further include a user guide describing the optimal reaction performance conditions. The guide is a printed document that explains how to use the kit, for example, the preparation method of PCR buffers, suggested reaction conditions and the like. The guide includes an information brochure in the form of pamphlets or leaflets, labels affixed to the kit, and instructions on the surface of a package containing the kit. In addition, the guide includes information that is disclosed or provided through electronic media such as the Internet.

Further, the present invention provides a composition for detecting *mycoplasma* infection, comprising:
a forward primer comprising a nucleotide sequence of SEQ ID NO: 1;
a forward primer comprising a nucleotide sequence of SEQ ID NO: 2;
a forward primer comprising a nucleotide sequence of SEQ ID NO: 3;
a forward primer comprising a nucleotide sequence of SEQ ID NO: 4;
a forward primer comprising a nucleotide sequence of SEQ ID NO: 5;
a forward primer comprising a nucleotide sequence of SEQ ID NO: 6;
a reverse primer comprising a nucleotide sequence of SEQ ID NO: 7;
a reverse primer comprising a nucleotide sequence of SEQ ID NO: 8; and
a reverse primer comprising a nucleotide sequence of SEQ ID NO: 9.

The present invention also provides a use of a primer set in detection or infection diagnosis of *mycoplasma*, the primer set comprising:
a forward primer comprising a nucleotide sequence of SEQ ID NO: 1;
a forward primer comprising a nucleotide sequence of SEQ ID NO: 2;
a forward primer comprising a nucleotide sequence of SEQ ID NO: 3;
a forward primer comprising a nucleotide sequence of SEQ ID NO: 4;
a forward primer comprising a nucleotide sequence of SEQ ID NO: 5;
a forward primer comprising a nucleotide sequence of SEQ ID NO: 6;
a reverse primer comprising a nucleotide sequence of SEQ ID NO: 7;
a reverse primer comprising a nucleotide sequence of SEQ ID NO: 8; and
a reverse primer comprising a nucleotide sequence of SEQ ID NO: 9.

Accordingly, the present invention provides a method for detecting *mycoplasma*, which can directly confirm whether a cell is infected with *mycoplasma*, by simultaneously amplifying DNA extracted by lysing a host cell infected with *mycoplasma* and DNA derived from mitochondria in the cytoplasm of a host cell. When conventional *mycoplasma* detection methods are used, DNA in a cell culture medium is used as a sample, and thus it is possible to confirm whether the medium has been infected with *mycoplasma*. However, according to the method of the present invention, the DNA of *mycoplasma* may be directly used as an amplification target so that detection sensitivity may be increased. In addition, since mitochondrial DNA in the host cell is used as the amplification target of an internal control sample, it is not only possible to easily confirm whether an appropriate amount of the sample is collected, but also the degree of the infection of *mycoplasma* may be quantitatively confirmed by comparing the band amounts between the internal control sample and the *mycoplasma* DNA.

Hereinafter, preferred examples are provided to help understanding the present invention. However, the following examples are merely provided to more easily understand the present invention, and the contents of the present invention are not limited by these examples.

Example 1

Preparation of *Mycoplasma*-Infected Cell Samples

Samples were prepared for cells and culture solutions used in the laboratory.

First, about 100 cells to be tested were obtained and placed in a PCR tube (Axygen; 14-222-261) with 150 µL of a culture solution, and centrifugation was performed for 1 minute to 2 minutes using a 500 rpm desktop centrifuge. The supernatant was removed, and 150 µL of PBS buffer (Hyclone; SH3025601) was added to the PCR tube where the precipitated cells remained. After mixing by tapping lightly with hand, centrifugation was performed again for 1 minute to 2 minutes using a 500 rpm desktop centrifuge. 5 μL of a DNA lysis buffer (composition: 0.2M Tris-HCl (pH 8.0), 0.1% Tween20, 0.1% NP40 and 2 mg/mL proteinase K) was added to the obtained cells, followed by mixing by tapping lightly with hand. Afterwards, the mixed solution was spin-down to separate into a supernatant and a precipitate layer, and then the supernatant was taken to perform Myco Pico prep (10 minutes at 65° C., 10 minutes at 95° C., and maintaining at 4° C.). Finally, the isolated and obtained DNA was dissolved in 5 μL of DEPC-DW and used as a PCR template for the next step.

The cultured medium sample to be tested was prepared by the same process as the *mycoplasma*-infected cell sample, but the sample was prepared by taking only the culture medium excluding the cells. The *mycoplasma*-negative cell pellet sample was also prepared by the same process as above, but samples were prepared for cells that were confirmed to be not infected with *mycoplasma* using a commercially available e-Myco™ *Mycoplasma* PCR Detection Kit (iNtRON biotechnology).

Example 2

Preparation of Primers for PCR for *Mycoplasma* Detection

PCR amplifying human mitochondrial DNA as a template were designed to amplify some portion of the COX1 gene (mt5718-mt6025) from the terminal portion of the TRNN gene in the human mitochondrial DNA sequence (internal control primer).

The internal control primer for amplifying mitochondrial DNA was prepared as an internal control primer mixture by diluting a forward primer and a reverse primer at a concentration of 10 μM each, followed by mixing the forward primer and the reverse primer at a ratio of 1:1 (w:w). As primers for detecting *mycoplasma*, a total of 6 forward primers were mixed with 10 μL each and filled with 40 μL of distilled water to prepare 100 μL of a forward primer mixture at a concentration of 60 μM. In addition, a total of 3 reverse primers were mixed with 10 μL each and filled with 70 μL of distilled water to prepare 100 μL of a reverse primer mixture at a concentration of 30 μM. Next, the forward primer mixture and the reverse primer mixture were mixed at a ratio of 1:1 (w:w) to prepare as a *mycoplasma* primer mixture.

TABLE 1

Primer sequences used in the present invention

| Target DNA | Name of primer | Sequence | Direction | SEQ ID NO. |
|---|---|---|---|---|
| Mycoplasma DNA | Myco-1_F | CGCCTGAGTAGTACGTTCGC | Forward | SEQ ID NO: 1 |
|  | Myco-2_F | CGCCTGAGTAGTACGTACGC | Forward | SEQ ID NO: 2 |
|  | Myco-3_F | TGCCTGAGTAGTACATTCGC | Forward | SEQ ID NO: 3 |
|  | Myco-4_F | TGCCTGGGTAGTACATTCGC | Forward | SEQ ID NO: 4 |
|  | Myco-5_F | CGCCTGGGTAGTACATTCGC | Forward | SEQ ID NO: 5 |
|  | Myco-6_F | CGCCTGAGTAGTATGCTCGC | Forward | SEQ ID NO: 6 |
|  | Myco-1_R | GCGGTGTGTACAAGACCCGA | Reverse | SEQ ID NO: 7 |
|  | Myco-2_R | GCGGTGTGTACAAAACCCGA | Reverse | SEQ ID NO: 8 |
|  | Myco-3_R | GCGGTGTGTACAAACCCCGA | Reverse | SEQ ID NO: 9 |
| mtDNA (Internal control primer) | Common Forward primers | GGCTTCAATCTACTTCTCCCG | Forward | SEQ ID NO: 10 |
|  | Common Reverse primers | AGCTCGGCTCGAATAAGGAG | Reverse | SEQ ID NO: 11 |

Primers for *mycoplasma* detection were prepared by dividing into two types. First, for primers for detecting the DNA of *mycoplasma*, 6 forward primers and 3 reverse primers of the sequences disclosed in [Table 1] below were designed by referencing already-known Non-Patent Document 1 and Non-Patent Document 2, and these primers target the 16s rRNA gene region that is specific to the genus *Mycoplasma*.

Next, in order to amplify the mitochondrial DNA of a host cell as an internal control sample for confirming the accuracy of the detection of *mycoplasma*, primers capable of Example 3

Performance of PCR Reaction for *Mycoplasma* Detection

In order to perform a PCR reaction, a PCR reaction solution was prepared first. The composition of the PCR reaction solution is as follows: 5 μL of Bioneer Accupower master mix (K-2609), 1 μL of the internal control primer mixture and 1 μL of the *mycoplasma* primer mixture.

7 μL of the PCR reaction solution and 3 μL of the *mycoplasma* DNA template sample (DNA concentration: 75 ng/μL to 90 ng/μL) prepared in [Example 1] above were mixed in a new PCR tube to perform a PCR reaction. Temperature and time conditions of the PCR are summarized in [Table 2] below.

TABLE 2

Temperature and time conditions of the PCR

| Step | Temperature (° C.) | Time |
|---|---|---|
| Initial denaturation | 95 | 2:00 min |
| 5 cycles | 94 | 0:30 sec |
|  | 50 | 0:30 sec |
|  | 72 | 1:00 min |
| 30 cycles | 94 | 0:15 sec |
|  | 56 | 0:15 sec |
|  | 72 | 1:00 min |
| Store | 4 | Infinity |

After completion of the PCR reaction, 3 μL to 10 μL of the PCR reaction product was loaded onto an agarose gel and subjected to electrophoresis at about 100 V for 20 minutes to 30 minutes to isolate DNA. The isolated DNA was observed on UV light to confirm the amplified DNA band.

Figure 1:
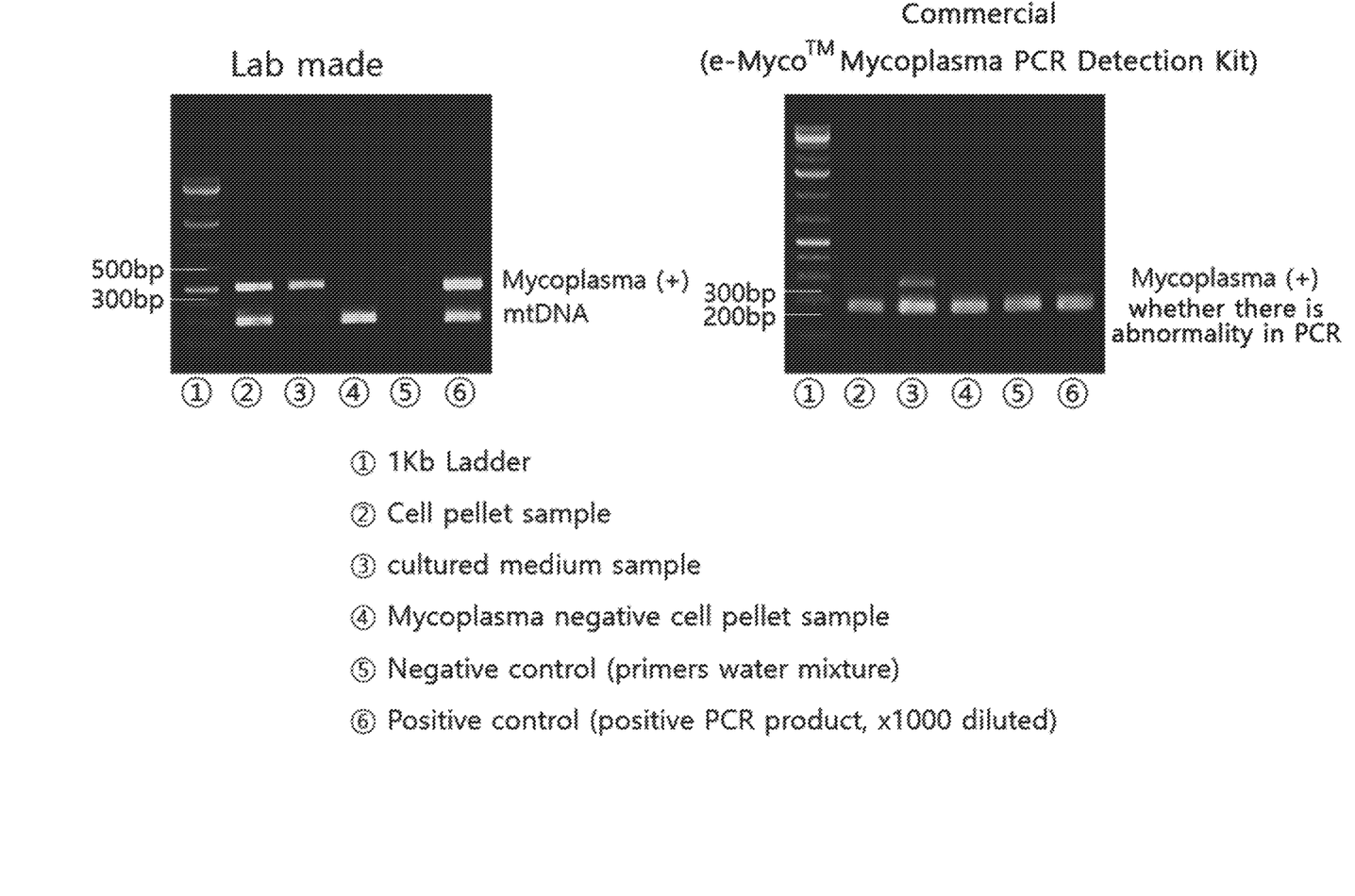
FIG. 1 illustrates the comparison between the electrophoresis results after performing PCR amplification by the *mycoplasma* detection method according to the present invention, and the electrophoresis results after performing PCR amplification according to the manufacturer's protocol using a commercial kit available on the market (e-Myco™ *Mycoplasma* PCR Detection Kit).

As a result, as shown in FIG. 1, in case of the experimental group (cell pellet sample) in which PCR was performed using DNA isolated from a host cell infected with mycoplasma as a template, it was confirmed that mycoplasma DNA was amplified and a DNA band having a size of 500 bp appeared, and at the same time, mitochondrial DNA of the host cell used as an internal control sample was also amplified and a DNA band having a size of 300 bp appeared.

In comparison, in case of the experimental group (cultured medium sample) in which PCR was performed under the same conditions using the culture medium of a host cell as a PCR template sample, it was confirmed that mycoplasma DNA was amplified and a DNA band of 500 bp was confirmed, but the mitochondrial DNA band of the host cell was not shown significantly.

In addition, in the non-infected control group (mycoplasma negative cell pellet sample) for a host cell not infected with mycoplasma, it was confirmed that only a DNA band having a size of 300 bp appeared, which was amplified by the internal control primer.

Example 4

Comparative Example: Mycoplasma Detection Experiment Using Commercial Kit Available on Market In order to compare with the method of the present invention, e-Myco™ Mycoplasma PCR Detection Kit (iNtRON biotechnology), which is a commercial kit available on the market, was used to perform a PCR reaction for mycoplasma detection according to the protocols provided by the manufacturer. DNA was isolated depending on the size by electrophoresis from the PCR amplification product, and the DNA band was observed on UV light.

As a result, as shown in FIG. 1, compared to the experimental group directly dealing with cells infected with mycoplasma, it was confirmed that a more significant DNA band appeared in the experimental group in which a PCR reaction was performed with a cultured medium, and it was confirmed that there was a concern that accuracy was reduced for confirming whether mycoplasma infection had occurred. In addition, it merely confirmed a DNA band of about 200 bp for confirming whether there was abnormality in the PCR, and since an internal control band did not appear, it was confirmed that the degree of mycoplasma infection could not be quantitatively confirmed.

Accordingly, the present invention provides a method for detecting mycoplasma, which can directly confirm whether a cell is infected with mycoplasma, by simultaneously amplifying DNA extracted by lysing a host cell infected with mycoplasma, and DNA derived from mitochondria in the cytoplasm of a host cell.

According to the method of the present invention, by directly using the DNA in a host cell, the DNA of mycoplasma bound around the nucleus of the host cell can be used directly as an amplification target, and thus detection sensitivity can be increased. In addition, since mitochondrial DNA in the host cell is used as the amplification target of an internal control sample, it is not only possible to easily confirm whether an appropriate amount of the sample is collected, but also the degree of mycoplasma infection can be quantitatively confirmed by comparing the band amounts between the internal control sample and mycoplasma DNA. Further, when the kit for detecting mycoplasma according to the present invention is used, it is possible to detect mycoplasma at a lower cost compared to various commercial mycoplasma detection kits that are currently available on the market.

What is claimed is:

1. A method for detecting *mycoplasma*, comprising:
   i) extracting DNA from a host cell isolated from a subject suspected of being infected with *mycoplasma*;
   ii) performing polymerase chain reaction (PCR) using the DNA extracted in step i) as a template; and
   iii) confirming a DNA band by electrophoresis of the PCR product performed in step ii),
   wherein the PCR of step ii) amplifies a target sequence using a primer set for amplifying *mycoplasma* DNA; and a primer set for amplifying mitochondrial DNA of a host cell, wherein the primer set for amplifying mitochondrial DNA of a host cell comprises: a forward primer comprising a nucleotide sequence of SEQ ID NO: 10; and a reverse primer comprising a nucleotide sequence of SEQ ID NO: 11.

2. The method of claim 1, wherein the host cell of step i) is a cell derived from human.

3. The method of claim 1, wherein the primer set for amplifying *mycoplasma* DNA comprises:
   a forward primer comprising a nucleotide sequence of SEQ ID NO: 1;
   a forward primer comprising a nucleotide sequence of SEQ ID NO: 2;
   a forward primer comprising a nucleotide sequence of SEQ ID NO: 3;
   a forward primer comprising a nucleotide sequence of SEQ ID NO: 4;
   a forward primer comprising a nucleotide sequence of SEQ ID NO: 5;
   a forward primer comprising a nucleotide sequence of SEQ ID NO: 6;
   a reverse primer comprising a nucleotide sequence of SEQ ID NO: 7;
   a reverse primer comprising a nucleotide sequence of SEQ ID NO: 8; and
   a reverse primer comprising a nucleotide sequence of SEQ ID NO: 9.

4. A method for providing information for diagnosing *mycoplasma* infection, comprising:
   i) extracting DNA from a host cell isolated from a subject suspected of being infected with *mycoplasma*;
   ii) performing polymerase chain reaction (PCR) using the DNA extracted in step i) as a template; and
   iii) determining that the subject is infected with *mycoplasma*, if the amplification of *mycoplasma* DNA is confirmed in the PCR of step ii),
   wherein the PCR of step ii) amplifies a target sequence using a primer set for amplifying *mycoplasma* DNA; and a primer set for amplifying mitochondrial DNA of a host cell, wherein the primer set for amplifying mitochondrial DNA of a host cell comprises: a forward primer comprising a nucleotide sequence of SEQ ID NO: 10; and a reverse primer comprising a nucleotide sequence of SEQ ID NO: 11.

5. The method of claim 4, wherein the PCR reaction of step ii) is performed using:
   a forward primer comprising a nucleotide sequence of SEQ ID NO: 1;
   a forward primer comprising a nucleotide sequence of SEQ ID NO: 2;
   a forward primer comprising a nucleotide sequence of SEQ ID NO: 3;
   a forward primer comprising a nucleotide sequence of SEQ ID NO: 4;
   a forward primer comprising a nucleotide sequence of SEQ ID NO: 5;
   a forward primer comprising a nucleotide sequence of SEQ ID NO: 6;
   a reverse primer comprising a nucleotide sequence of SEQ ID NO: 7;
   a reverse primer comprising a nucleotide sequence of SEQ ID NO: 8;

a reverse primer comprising a nucleotide sequence of SEQ ID NO: 9;
a forward primer comprising a nucleotide sequence of SEQ ID NO: 10; and
a reverse primer comprising a nucleotide sequence of SEQ ID NO: 11.

6. The method of claim 4, wherein the confirmation of the amplification of *mycoplasma* DNA in step iii) confirms that DNA having a size of 500 bp has been amplified.

7. A kit for detecting *mycoplasma*, comprising:
a) a cell lysis buffer;
b) a primer set for amplifying *mycoplasma* DNA; and
c) a primer set for amplifying mitochondrial DNA of a host cell, wherein the primer set for amplifying mitochondrial DNA of a host cell comprises:
a forward primer comprising a nucleotide sequence of SEQ ID NO: 10; and
a reverse primer comprising a nucleotide sequence of SEQ ID NO: 11.

8. The kit of claim 7, wherein the b) primer set for amplifying *mycoplasma* DNA comprises:
a forward primer comprising a nucleotide sequence of SEQ ID NO: 1;
a forward primer comprising a nucleotide sequence of SEQ ID NO: 2;
a forward primer comprising a nucleotide sequence of SEQ ID NO: 3;
a forward primer comprising a nucleotide sequence of SEQ ID NO: 4;
a forward primer comprising a nucleotide sequence of SEQ ID NO: 5;
a forward primer comprising a nucleotide sequence of SEQ ID NO: 6;
a reverse primer comprising a nucleotide sequence of SEQ ID NO: 7;
a reverse primer comprising a nucleotide sequence of SEQ ID NO: 8; and
a reverse primer comprising a nucleotide sequence of SEQ ID NO: 9.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Myco-1_F

<400> SEQUENCE: 1
cgcctgagta gtacgttcgc                    20

<210> SEQ ID NO 2
<211> LENGTH: 20
<212> TYPE: DNA
<213> ORGANISM: Artificial
<220> FEATURE:
<223> OTHER INFORMATION: Myco-2_F -continued

<400> SEQUENCE: 2
cgcctgagta gtacgtacgc                                                  20

<210> SEQ ID NO 3
<211> LENGTH: 20
<212> TYPE: DNA
<213> ORGANISM: Artificial
<220> FEATURE:
<223> OTHER INFORMATION: Myco-3_F

<400> SEQUENCE: 3
tgcctgagta gtacattcgc                                                  20

<210> SEQ ID NO 4
<211> LENGTH: 20
<212> TYPE: DNA
<213> ORGANISM: Artificial
<220> FEATURE:
<223> OTHER INFORMATION: Myco-4_F

<400> SEQUENCE: 4
tgcctgggta gtacattcgc                                                  20

<210> SEQ ID NO 5
<211> LENGTH: 20
<212> TYPE: DNA
<213> ORGANISM: Artificial
<220> FEATURE:
<223> OTHER INFORMATION: Myco-5_F

<400> SEQUENCE: 5
cgcctgggta gtacattcgc                                                  20

<210> SEQ ID NO 6
<211> LENGTH: 20
<212> TYPE: DNA
<213> ORGANISM: Artificial
<220> FEATURE:
<223> OTHER INFORMATION: Myco-6_F

<400> SEQUENCE: 6
cgcctgagta gtatgctcgc                                                  20

<210> SEQ ID NO 7
<211> LENGTH: 20
<212> TYPE: DNA
<213> ORGANISM: Artificial
<220> FEATURE:
<223> OTHER INFORMATION: Myco-1_R

<400> SEQUENCE: 7
gcggtgtgta caagacccga                                                  20

<210> SEQ ID NO 8
<211> LENGTH: 20
<212> TYPE: DNA
<213> ORGANISM: Artificial
<220> FEATURE:
<223> OTHER INFORMATION: Myco-2_R

<400> SEQUENCE: 8
gcggtgtgta caaacccga                                                   20

<210> SEQ ID NO 9

```
<211> LENGTH: 20
<212> TYPE: DNA
<213> ORGANISM: Artificial
<220> FEATURE:
<223> OTHER INFORMATION: Myco-3_R

<400> SEQUENCE: 9
gcggtgtgta caaaccccga                                                    20

<210> SEQ ID NO 10
<211> LENGTH: 21
<212> TYPE: DNA
<213> ORGANISM: Artificial
<220> FEATURE:
<223> OTHER INFORMATION: Common Forward primer

<400> SEQUENCE: 10
ggcttcaatc tacttctccc g                                                  21

<210> SEQ ID NO 11
<211> LENGTH: 20
<212> TYPE: DNA
<213> ORGANISM: Artificial
<220> FEATURE:
<223> OTHER INFORMATION: Common Reverse primer

<400> SEQUENCE: 11
agctcggctc gaataaggag                                                    20
```